(12) United States Patent
Sigg et al.

(10) Patent No.: US 7,778,705 B2
(45) Date of Patent: Aug. 17, 2010

(54) ELECTRONIC AND BIOLOGICAL PACEMAKER SYSTEMS

(75) Inventors: Daniel C. Sigg, St. Paul, MN (US); Timothy G. Laske, Shoreview, MN (US); Vinod Sharma, Blaine, MN (US); Orhan Soykan, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 867 days.

(21) Appl. No.: 11/554,770

(22) Filed: Oct. 31, 2006

(65) Prior Publication Data

US 2008/0103537 A1 May 1, 2008

(51) Int. Cl.
*A61N 1/00* (2006.01)

(52) U.S. Cl. .............................. 607/9; 607/3
(58) Field of Classification Search ................ 607/2–28
See application file for complete search history.

(56) References Cited

U.S. PATENT DOCUMENTS

| 5,103,821 | A | 4/1992 | King |
| 6,690,970 | B1 | 2/2004 | Taheri et al. |
| 6,776,987 | B1 | 8/2004 | Edelberg et al. |
| 6,849,611 | B2 | 2/2005 | Rosen et al. |
| 2004/0214182 | A1 | 10/2004 | Sharma et al. |
| 2004/0254134 | A1 | 12/2004 | Marban et al. |
| 2005/0021089 | A1 | 1/2005 | Sharma |
| 2005/0244377 | A1 | 11/2005 | Sigg et al. |

FOREIGN PATENT DOCUMENTS

WO WO02/087419 A 11/2002
WO WO2005/062958 A 7/2005

OTHER PUBLICATIONS

Bucchi Annalisa et al; "Wild-Type and Mutant HCN Channels in a Tandem Biological-Electronic Cardiac Pacemaker"; Circulation, Lippincot Williams and Wilkins, Baltimore, US, vol. 114, No. 10, Sep. 2006, pp. 992-999.

*Primary Examiner*—Scott M Getzow
(74) *Attorney, Agent, or Firm*—Stephen W. Bauer

(57) ABSTRACT

Heart pacing systems include at least one electronic or biological pacemaker as a primary pacemaker, and at least one electronic or biological pacemaker as a backup pacemaker. When implanted, the primary pacemaker(s) produce primary pacing stimuli that modulate cardiac function. The backup pacemaker(s) provide backup pacing stimuli when the electronic pacemaker is unable to modulate cardiac function at the predetermined pacing rate. The heart pacing systems are implemented by implantation in regions where they can provide pacing stimuli to cardiac tissue.

14 Claims, 5 Drawing Sheets

ELECTRONIC AND BIOLOGICAL PACEMAKER SYSTEMS

FIELD OF THE INVENTION

The present invention relates to systems, compositions, and methods for providing curative therapy for cardiac dysfunction, and particularly relates to systems, compositions, and methods that include or introduce biological curative therapeutic agents and electronic implantable pacemakers for treating arrhythmias and cardiac pacing dysfunction.

BACKGROUND OF THE INVENTION

Cardiac contraction in a healthy human heart is initiated by spontaneous excitation of the sinoatrial ("SA") node, which is located in the right atrium. The electric impulse generated by the SA node travels to the atrioventricular ("AV") node where it is transmitted to the bundle of His and to the Purkinje network. The fibers in the Purkinje network branch out in many directions to facilitate coordinated contraction of the left and right ventricles, thus providing natural pacing. In some disease states, the heart loses some of its capacity to pace properly. Such dysfunction is commonly treated by implanting a pacemaker.

While effectively improving the lives of many patients, implantable pacemakers rely on a self-contained power source such as a battery and consequently have a limited lifetime before the power source is in need of replacement. Hence, an otherwise healthy patient may require multiple surgeries to replace the power source or the entire implantable pacemaker. In addition, implantable pacemaker batteries are large and are usually the bulkiest pacemaker component. A pacemaker's size and capability for implantation in different body regions are typically dictated by the battery size. Also, implantable pacemakers have very limited or no capacity for directly responding to the body's endogenous signaling the way the SA node responds to such signaling, i.e. by a modulation of the heart rate relative to the physiological and emotional state (e.g. sleep, rest, stress, exercise).

Recently, biological methods of influencing a patient's cardiac cells have been developed, some of which include administering biopharmaceutical compositions that affect cardiac pacing. Developments in genetic engineering have produced methods for genetically modifying cardiac cells to convert non-pacemaking cardiac cells to cardiac cells. For example, U.S. Pat. No. 6,214,620 describes a method for modulating the excitability of ventricular cells by controlling the regulation of the expression of certain ion channels (e.g. $K^+$ channels). PCT Publication No. WO 02/087419 and WO 05/062890A3 describe methods and systems for modulating electronic behavior of cardiac cells by genetic modification of inwardly rectifying $K^+$ channels ($I_{K1}$) in quiescent ventricular cells. PCT Publication No. WO 02/098286 and WO 05/062958A2 describe methods for regulating pacemaker function of cardiac cells with HCN molecules (HCN 1, 2, 3 or 4 isoforms of the pacemaker current $I_f$). It is thought that these and other biological methods and systems may be used as stand-alone cardiac therapies. However, to ensure continuing proper cardiac function, U.S. Publication No. US 2004/0215251 discloses the use of an implantable electric pacemaker as a backup pacing device, with a biological pacemaker expressing features that regulate the primary pacing functions. A need remains, however, for implementations of a biological pacemaker system, alone or in cooperation with an implantable electronic pacemaker, which provides additional safeguards that will ensure successful curative therapy for cardiac dysfunction. A need also remains for the use of biological pacemakers as a means for reducing the overall size of an implantable electric pacemaker.

BRIEF SUMMARY OF THE INVENTION

According to one embodiment, a heart pacing system includes at least one electronic pacemaker and at least one biological pacemaker. When implanted, the electronic pacemaker(s) produce primary pacing stimuli that modulate cardiac function. The biological pacemaker(s) are functionally suppressed when the electronic pacemaker is modulating cardiac function at a predetermined pacing rate. The biological pacemaker(s) also provide backup pacing stimuli when the electronic pacemaker is unable to modulate cardiac function at the predetermined pacing rate.

According to another embodiment, a heart pacing system includes at least one primary biological pacemaker and at least one backup biological pacemaker. When implanted, the primary biological pacemaker(s) produce primary pacing stimuli to modulate cardiac function. The backup biological pacemaker(s) are suppressed when the primary biological pacemaker is modulating cardiac function at a predetermined pacing rate, and also produce backup pacing stimuli when the primary biological pacemaker is unable to modulate cardiac function at the predetermined pacing rate.

According to another embodiment, a heart pacing system includes at least one biological pacemaker as a primary pacemaker, and an electronic pacemaker as a backup to the biological pacemaker(s). When implanted, the biological pacemaker(s) produce primary pacing stimuli to modulate cardiac function, and the electronic pacemaker produces backup pacing stimuli that modulate cardiac function when the at least one biological pacemaker is unable to modulate cardiac function at a predetermined pacing rate. The electronic pacemaker includes an interior volume that is between less than 6.0 $cm^3$, and less than 1.0 $cm^3$.

Methods are also provided for implementing each of the heart pacing systems. The method includes implanting each of the electric and/or biological pacemakers in regions where they can provide pacing stimuli to cardiac tissue.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
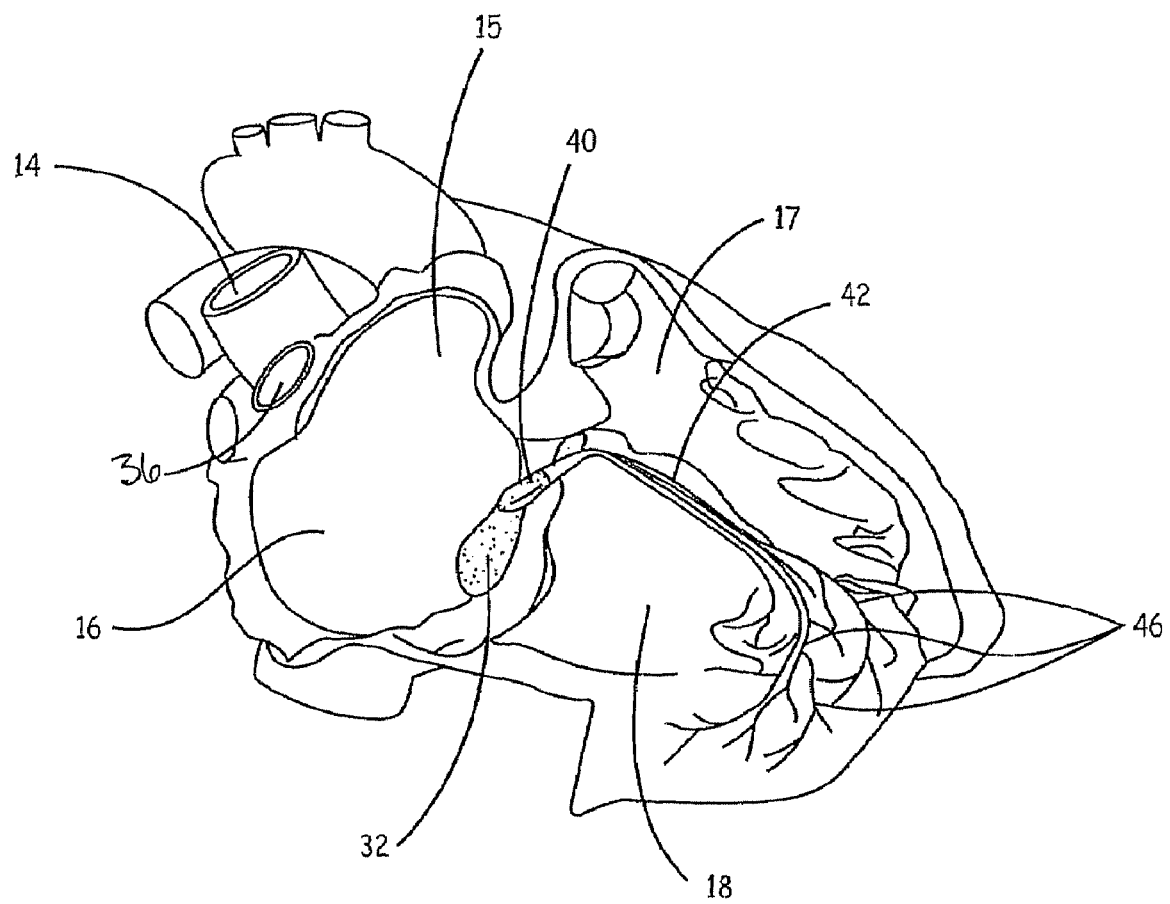
FIG. 1 is side view of the right side of a heart having an anterior-lateral wall peeled back to present a portion of a heart's intrinsic conduction system and chambers of a right atrium and a right ventricle.

FIG. 1 is side view of the right side of a heart having an anterior-lateral wall peeled back to present a portion of a heart's intrinsic conduction system and chambers of a right atrium 16 and a right ventricle 18. Pertinent elements of the heart's intrinsic conduction system include the SA node 36, the AV node 32, the bundle of His 40, the right bundle branch 42, and the Purkinje fibers 46. The left bundle branch is not depicted. The SA node 36 is shown at a junction between a superior vena cava 14 and the right atrium 16. An electric impulse initiated at the SA node 36 travels rapidly through the right atrium 16 and the non-illustrated left atrium to the AV node 32. At the AV node 32, the impulse slows to create a delay before passing on through the bundle of His 40, which branches, in an interventricular septum 17, into the right bundle branch 42 and the non-illustrated left bundle branch and then into the Purkinje fibers 46. The impulse then travels rapidly throughout the right ventricle 18 and the non-illustrated left ventricle. This electric impulse flow creates an orderly sequence of atrial and ventricular contraction to efficiently pump blood through the heart. If a portion of the heart's intrinsic conduction system becomes dysfunctional, efficient pumping is compromised.

A patient whose SA node 36 has become dysfunctional may be implanted with a pacemaker, which often includes placing lead electrodes in the right atrial appendage 15. The lead electrodes stimulate the right atrium 16 downstream of the dysfunctional SA node 36, and the stimulating pulse travels on to the AV node 32, the bundle of His 40, and the Purkinje fibers 46 to restore physiological contraction of the heart at a regular and physiological rate.

Figure 2:
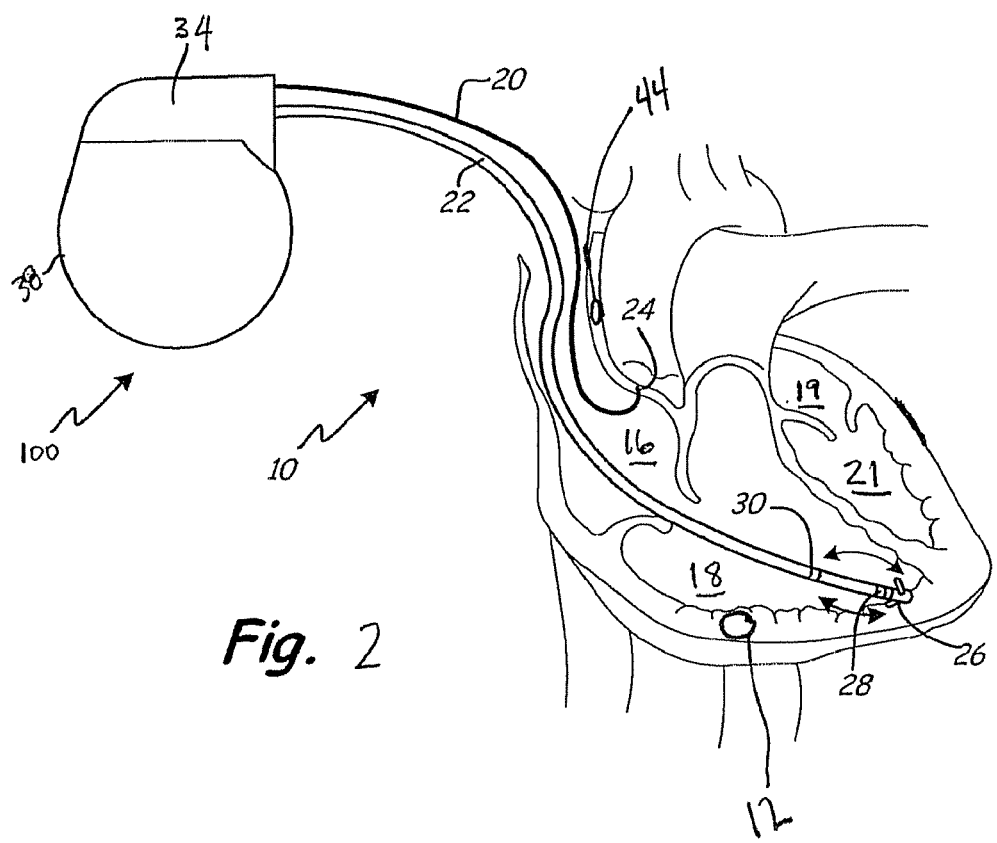
FIG. 2 is a side view of an implantable pacemaker illustrated in its functional relation to a heart, which is depicted in cross-section to reveal a plurality of biological pacemakers implanted in some of its chambers according to an embodiment of the invention.

Turning now to FIG. 2, a backup pacing system 10 is depicted, including a side view of an electronic implantable pacemaker 100 illustrated in its functional relation to a heart, which is depicted in cross-section to reveal the right atrium 16, the left atrium 19, the right ventricle 18, and the left ventricle 21. The depicted implantable pacemaker 100 includes a housing or can 38, a header 34, a right atrial lead 20, and a right ventricular lead 22. The atrial lead 20 extends from the header 18 to the right atrium 16. An electrode 24 carried at a distal end of the atrial lead 20 contacts a wall of the right atrium 16. The right ventricular lead 22 includes a distal fixation device 26, a distal tip electrode 28, and a ring electrode 30. Also depicted is a ventricular biological pacemaker 12, which is implanted in a wall of the right ventricle 18 and either performs a primary pacing function or is available as a backup to the implantable pacemaker 100, and specifically to the pacing functions performed by the right ventricular lead 22. Although the biological pacemaker 12 is depicted as being implanted in the wall of the right ventricle, other suitable and perhaps preferable implantation locations include the epicardial wall of the left ventricle and the interventricular septum. Furthermore, an atrial biological pacemaker 44 is implanted in a wall of the right atrium 16 and also either performs a primary pacing function or is available as a backup to the implantable pacemaker 100, and specifically to the pacing functions performed by the atrial lead 20. Although two biological pacemakers 12 and 44 are depicted, it will be appreciated that fewer or more than two biological pacemakers may be employed, and implanted in different heart locations, according to the heart condition and the desired therapy. Furthermore, although in the depicted embodiment both the atrial lead 20 and the right ventricular lead 22 are utilized, fewer or more than two leads may be necessary according to the heart condition and the desired therapy.

The functions and implementations of the implantable pacemaker 100 and the biological pacemakers 12 and 44 will next be described. Atrioventricular (AV) sequential pacing is achieved using the implantable pacemaker 100 by transmitting pacing stimuli to the right atrium 16 and the right ventricle 18. Within the housing 38 is a power source such as a battery, power supply circuitry, sensing and signal processing circuitry, therapy delivery circuitry (which may include pacing as well as cardioversion/defibrillation circuitry), a microprocessor and associated memory, and telemetry circuitry. Atrial stimulation is transmitted to the right atrium 16 through the atrial lead 20 and its associated electrode 24. Pacing stimulation for the right ventricle 18 includes electric pulses that are applied using the tip electrode 28 and the ring electrode 30. The pacing circuitry, including sensing and signal processing circuitry inside the housing 38, generates the pacing pulses delivered through the leads 20 and 22 to the right atrium 16 and the right ventricle 18, respectively. The electrodes 24, 28, and 30 are also used together with the pacing circuitry to derive sensed signals representing the heart's electric activity.

As used herein, the term "biological pacemaker" refers to a polynucleotide composition, or a cell-based composition including such as ones having a specific modified or unmodified polynucleotide composition, for modulating cardiac contraction to desired levels. Polynucleotides of choice can be made by traditional PCR-based amplification and known cloning techniques. Alternatively, a polynucleotide of the invention can be made by automated procedures that are well known in the art. A polynucleotide of the invention should include a start codon to initiate transcription and a stop codon to terminate translation. Suitable polynucleotides for use with the invention can be obtained from a variety of public sources including, without limitation, GenBank (National Center for Biotechnology Information (NCBI)), EMBL data library, SWISS-PROT (University of Geneva, Switzerland), the PIR-International database; and the American Type Culture Collection (ATCC)(10801 University Boulevard, Manassas, Va. 20110-2209). See generally, Benson, D. A. et al, *Nucl. Acids. Res.*, 25:1 (1997) for a description of GenBank. The particular polynucleotides useful with the present invention are readily obtained by accessing public information from GenBank.

Any suitable DNA vector or delivery vehicle may be utilized to transfer the desired nucleotide sequence to the targeted cardiac cells. For example, the nucleotide sequence may be cloned into a viral vector such as an adenoviral associated vector (AAV) or other viral vectors such as herpes vectors, and retroviral vectors such as lentiviral vectors. The type of viral vector selected is dependent on the target tissue and the length of the sequence to be delivered. For a discussion of viral vectors see *Gene Transfer and Expression Protocols*, Murray ed., pp. 109-206 (1991). Alternatively, non-viral delivery systems may be utilized. For example, liposome:DNA complexes, plasmid:liposome complexes, naked DNA, DNA-coated particles, or polymer based systems may be used to deliver the desired sequence to the targeted cardiac cells. The above-mentioned delivery systems and protocols therefore are described in *Gene Targeting Protocols*, Kmeic 2ed. pp. 1-35 (2002), and *Gene Transfer and Expression Protocols*, Vol. 7, Murray ed. pp 81-89 (1991).

AAV vectors can be constructed using techniques well known in the art. Typically, the vector is constructed so as to provide operatively linked components of control elements. For example, a typical vector includes a transcriptional initiation region, a nucleotide sequence of the protein to be expressed, and a transcriptional termination region. Typically, such an operatively linked construct will be flanked at its 5' and 3' regions with AAV ITR sequences, which are required viral cis elements. The control sequences can often be provided from promoters derived from viruses such as, polyoma, Adenovirus 2, cytomegalovirus, and Simian Virus 40. Viral regulatory sequences can be selected to achieve a high level of expression in a variety of cells. Alternatively, ubiquitously expressing promoters, such as the early cytomegalovirus promoter can be utilized to accomplish expression in any cell type. A third alternative is the use of promoters that drive tissue specific expression. This approach is particularly useful where expression of the desired protein in non-target tissue may have deleterious effects. Thus, according to another preferred embodiment, the vector contains the proximal human brain natriuretic brain (hBNP) promoter that functions as a cardiac-specific promoter. For details on construction of such a vector see LaPointe et al., *Left Ventricular Targeting of Reporter Gene Expression In Vivo by Human BNP Promoter in an Adenoviral Vector*, Am. J. Physiol. Heart Circ. Physiol., 283:H1439-45 (2002).

Vectors may also contain cardiac enhancers to increase the expression of the transgene in the targeted regions of the cardiac conduction system. Such enhancer elements may include the cardiac specific enhancer elements derived from Csx/Nkx2.5 regulatory regions disclosed in the published U.S. Patent Application 20020022259, the teachings of which are herein incorporated by reference.

Therapeutic methods of the present invention include delivery of an effective amount of a genetic construct or genetically engineered cells or unmodified cells with pacemaking activity to the cardiac cells to produce a biological pacemaker that increases the intrinsic pacing rate of such cells. The implantable pacemaker 100 is used in tandem with the biological pacemaker according to one embodiment, although in subsequently described embodiments an implantable pacemaker is not included. The biological pacemakers 12 and 44 may be introduced using genetically engineered vectors, genetically engineered cells, or unmodified cells, which are implanted at a selected location. One delivery method includes the use of a delivery tool, such as a catheter having electric sensing capabilities, which is introduced directly into either the right atrium 16 or the right ventricle 18, as just a couple of examples. The delivery tool may include electrodes for sensing electric activity and delivering pacing stimuli in order to determine the desired location for the biological pacemakers 12 and 44. Once the location is determined, genetically engineered viruses, gene-modified cells or unmodified cells are delivered to the myocardium at that location to form a biological pacemaker. The delivery tool may include an injection device that injects the viruses or cells into the myocardium. One suitable method for injecting a genetic construct directly into the myocardium is described by R. J. Guzman et al., *Circ. Res.*, 73:1202-1207 (1993). Furthermore, a delivery system for delivering genetic material to a targeted heart region is described in U.S. Pat. No. 7,103,418 and PCT Publication No. WO 98/02150, the teachings of which are incorporated herein by reference. Alternatively, genetically engineered cells may be cultured and proliferated on a solid scaffold, and then surgically delivered to the selected heart region together with the scaffold. The scaffold may also be directly injected into the myocardium.

Perfusion protocols that are useful with the inventive methods are often sufficiently capable of delivering a genetic construct to at least about 10% of cardiac myocytes. Infusion volumes of between about 0.01 ml and about 1 ml are useful for direct intramyocardial injection. Also, suitable methods for targeting non-viral vector genetic constructs to the heart are described in U.S. Pat. No. 6,376,471, the teachings of which are hereby incorporated by reference.

When a genetic construct (in contrast to genetically engineered cells or unmodified cells) is introduced to the myocardium using any suitable technique, the genetic material is delivered into the cells by, for example, transfection or transduction procedures. Transfection and transduction refer to the acquisition by a cell of new genetic material by incorporation of added nucleic acid molecules. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection (commonly known as lipofection). Transduction refers to the process of transferring nucleic acid into a cell using a DNA or RNA virus. Suitable viral vectors for use as transducing agents include, but are not limited to, retroviral vectors, adeno-associated viral vectors, lentiviral vectors, herpes simplex viral vectors, vaccinia viruses, and Semliki Foret virus vectors.

Depending on the type of biological pacemaker and the heart condition, it may take from days to weeks after implantation before transfected or genetically engineered cells express their pacing functions. Furthermore, in some cases an electronic implantable pacemaker may be more effective than a biological pacemaker for a particular heart condition. For these reasons, in one exemplary system the implantable pacemaker 100 is implemented to perform backup pacing functions. For example, in the event that one or more of the biopacemakers 12 and 44 fail or malfunction, or if a slowing in the pacing rate is sensed, the implantable pacemaker 100 may be automatically activated to assume the pacing function. Additionally, the implantable pacemaker 100 may supplement the activity of one or more of the biopacemakers 12 and 44 in the event that either one fails to produce sufficient stimulation. As a specific example, if the atrial biological pacemaker 44 fails and the ventricular biological pacemaker 12 is functional, then the electronic pacemaker 100 is activated to pace the atrium. The electronic pacemaker 100 maintains atrial pacing at the ventricular biological pacemaker rate, and atrial pacing pulse is timed 100-200 ms prior to the anticipated ventricular excitation to produce the necessary atrial kick and optimal filling of the ventricles.

Figure 4:
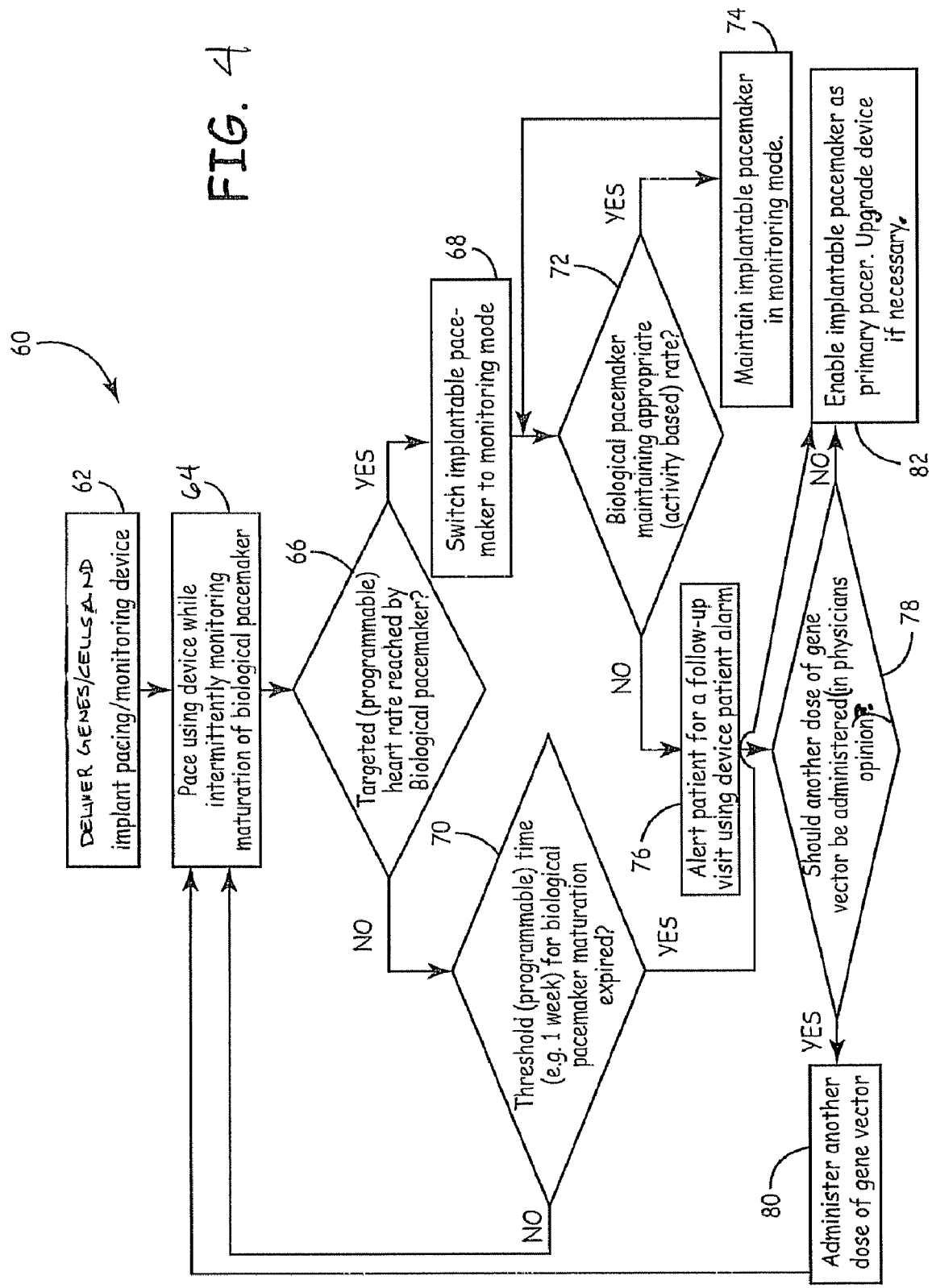
FIG. 4 is a flow chart depicting a method for coordinating the operation of a biological pacemaker and an implantable pacemaker according to an embodiment in which the biological pacemaker performs primary pacing functions and the implantable pacemaker serves as a backup pacing apparatus.

An exemplary method of performing pacing functions on a heart using the implantable pacemaker 100 and one or more of the biopacemakers 12 and 44 is depicted in the flow chart of FIG. 4. The method 60 includes, as step 62, delivering a gene vector or genetically modified or unmodified cells to a targeted region of the cardiac conduction system, and implanting an electronic pacemaker and monitoring device. As step 64, the electronic pacemaker is used to pace the patient's heart while computer-implemented software intermittently monitors the maturation of the biopacemaker. Monitoring the biopacemaker may be performed by simply comparing the present heart rhythm with the predetermined heart rhythm that the biopacemaker is targeted to produce. As step 66, the computer-implemented software makes a determination of whether the targeted heart rate is produced by the biopacemaker. If the targeted or programmable heart rate has been reached, the electronic pacemaker is switched to a monitoring mode as step 68. However, if the targeted heart rate has not been reached by the biological pacemaker, then as step 70, the computer-implemented software determines whether a predetermined biopacemaker maturation time has expired. If the time has expired, then the electronic pacemaker is enabled as the primary pacemaker as step 82. If, on the other hand, the predetermined time for the biological pacemaker has not expired, the method reverts back to step 64 and pacing is performed by the electronic pacemaker while continuing to intermittently monitor maturation of the biological pacemaker. Returning now to step 66, if the targeted heart rate is produced by the biopacemaker, then as step 68 the electronic pacemaker is switched to simply monitor the operation of the biological pacemaker by comparing the present heart rhythm with the predetermined heart rhythm that the biopacemaker is targeted to produce. All monitoring information from the electronic pacemaker may be wirelessly transmitted, according to a programmed reporting regimen or upon a user command, to a remote communication hub for review by a concerned health professional. Determinations including diagnoses and appropriate therapies may be made based on the monitoring information.

While monitoring the biopacemaker, the computer-implemented software determines as step 72 whether the biopacemaker is maintaining the targeted heart rate. According to an exemplary embodiment, monitoring by the electronic pacemaker also includes screening the patient's activity level and correlating the activity level with an appropriate heart rate. If the appropriate pacing rate is maintained by the biopacemaker, the implantable pacemaker remains in the monitoring mode as step 74. If the biopacemaker is not maintaining the appropriate rate, an alert is triggered as step 76 to make the patient aware of the need to consult with a physician as part a follow-up visit. The alert may be communicated by suitable perceptible means including an audible alarm. Further, as step 78, a determination is made of whether another dose of gene vector or genetically-modified cells should be administered. This determination is typically made by the physician. If additional genes or genetically-modified or unmodified cells are deemed necessary, another dose is administered as step 80, and the method reverts back to step 64 for pacing to be performed using the electric pacemaker while intermittently monitoring the maturation of the biopacemaker. In the alternate, if the administration of another dose of gene vector is not necessary or advisable, the method reverts to step 82 and the implantable pacemaker continues to operate as the primary pacer.

In the context of the present invention, electrophysiological assay methods are employed to detect modulation of cells in the heart's conduction system and thereby determine the heart rate. For example, such methods are useful as the basis for executing the previously-described method steps 66 and 72 of making heart rate-based determinations using computer-implemented software included as part of the implantable medical device 100, for example. However, according to other embodiments such as those subsequently described in which no implantable pacemaker is employed, the assaying methods may be performed using an external apparatus. The particular electrophysiological assay methods include conventional tests for determining cardiac action potential characteristics, such as action potential duration (APD). An example of a method related to performing such tests is disclosed by Josephson M E, *Clinical Cardiac Electrophysiology: Techniques and Interpretations*, Lea & Febiger. (1993), pp 22:70, the teachings of which are herein incorporated herein by reference. Alternatively, an electrophysiological mapping catheter may be inserted into the cardiac chamber, and the signals produced thereby may then be reviewed using standard EGM mapping methods to determine the function and site of pacemaker origination. Advanced electro-anatomical mapping methods may also be used to obtain electro-anatomical and electrophysiological maps of conduction and activation. Briefly, a standard electrophysiological assay includes the following steps: delivering to the heart a genetic construct or modified and/or unmodified cells of the invention, transferring the genetic construct and/or modified and/or unmodified cells into the heart under conditions which can allow expression of an encoded amino acid sequence; and detecting increase of at least one electric property in the cells of the heart to which the genetic construct and/or modified cells were delivered, wherein at least one property is the pacing rate of the cells, relative to a baseline value. Baseline values will vary with respect to the particular target region chosen in the conduction system. Additionally, modulation of cardiac electric properties obtained with the methods of the invention may be observed by performing a conventional electrocardiogram (ECG) before and after administration of the genetic construct of the invention and inspecting the ECG results. ECG patterns from a heart's electric excitation have been well studied. Various methods are known for analyzing ECG records to measure changes in the electric potential in the heart associated with the spread of depolarization and repolarization through the heart muscle.

Figure 5:
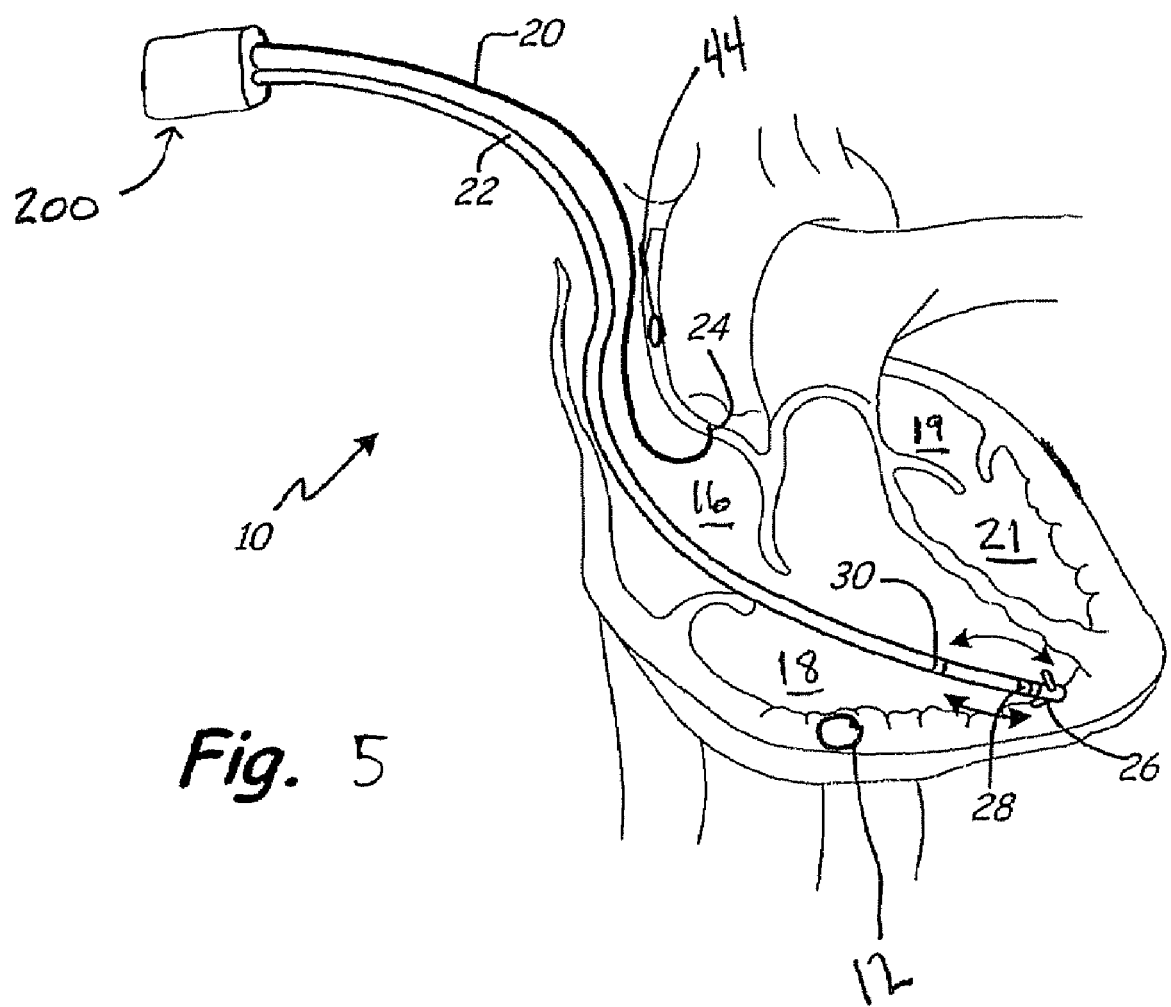
FIG. 5 is a side view of a miniaturized implantable pacemaker illustrated in its functional relation to a heart, which is depicted in cross-section to reveal a plurality of biological pacemakers implanted in some of its chambers according to an embodiment of the invention.

FIG. 5 is a side view of a miniaturized electronic pacemaker 200 illustrated in its functional relation to a heart, which is depicted in cross-section to reveal a plurality of biological pacemakers implanted in some of its chambers according to an embodiment of the invention. As previously mentioned, conventional implantable pacemaker batteries are large and are usually the bulkiest pacemaker component. A pacemaker's size and capability for implantation in different body regions are typically dictated by the battery size. With the implantable pacemaker 200 of the present invention being used only for backup pacing functions, the need for a large battery is eliminated. This is because during normal heart rhythm, or hearth rhythm prescribed by the at least one biological pacemaker, power from the implantable pacemaker battery is only expended on one or more minor functions such as device maintenance functions, sensory functions, rescue pacing as necessary, and alerting functions if the at least one biological pacemaker is not functioning properly. Consequently, the size of the implantable pacemaker of the present invention is drastically reduced when compared with conventional implantable pacemakers. According to an exemplary embodiment, the implantable pacemaker 200 has an interior volume ranging between 0.3 cm$^3$ and 6.0 cm$^3$, and preferably has an interior volume that is less than 1.0 cm$^3$.

According to another embodiment, the implantable pacemaker 100 assumes primary pacing functions, and the biological pacemakers 12 and 44 are available to perform backup or rescue pacing functions. For example, if the SA node 36 becomes diseased or for some reason experiences SA node arrest, the implantable pacemaker 100 may be unable to adequately create an impulse that will travel along the conduction pathway. As another example, the implantable pacemaker 100 may experience a failure due to battery depletion or equipment breakdown. In such an event, one or more of the implanted biological backup pacemakers 12 and 44 will become the dominant pacemakers to produce a hearth rhythm at a sufficient pace to prevent cardiac arrest and/or cardiovascular symptoms and/or Adam-Stokes-Attacks.

Figure 3:
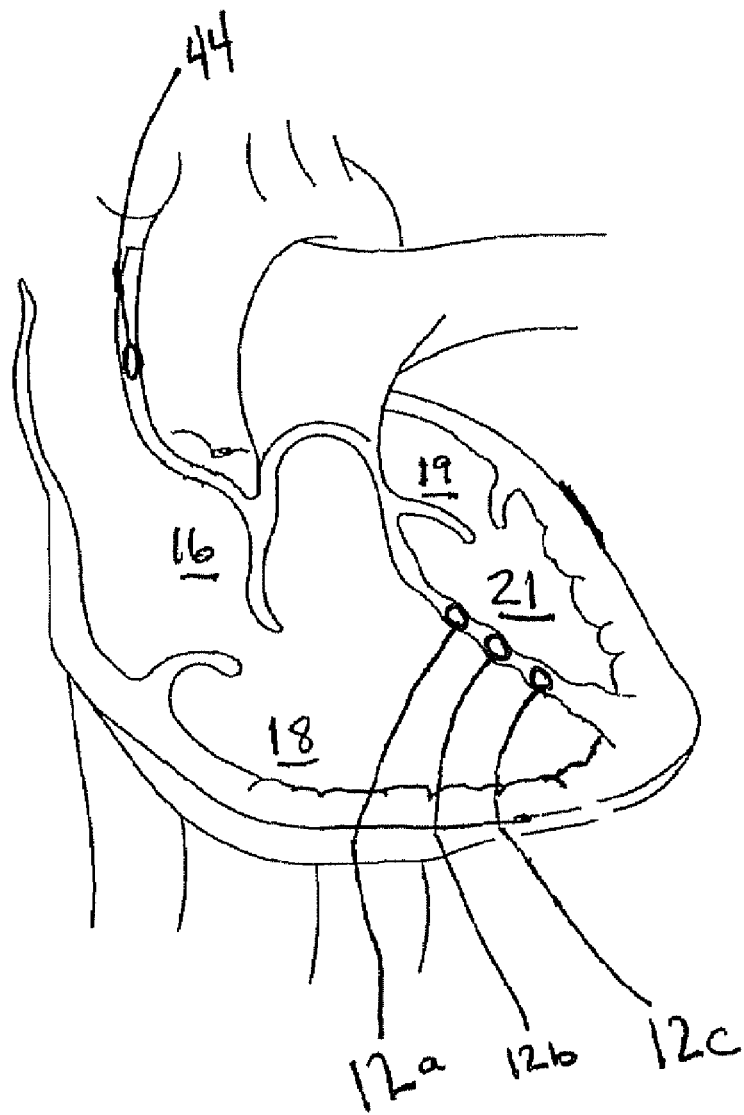
FIG. 3 is a cross-sectional view of a heart having a plurality of biological pacemakers implanted in the right ventricle and the right atrium according to an embodiment of the invention.

According to another embodiment, both primary and backup pacing is performed using biological pacemakers, effectively removing any need for the previously-discussed implantable pacemaker. FIG. 3 depicts a heart, which is illustrated as a cross-sectional view to reveal the right atrium 16, the left atrium 19, the right ventricle 18, and the left ventricle 21. Implanted into a wall of the right ventricle 18 is a plurality of ventricular biological pacemakers 12a to 12c, and an atrial biological pacemaker 44 implanted in a wall of the right atrium 16. Although three ventricular biological pacemakers 12a to 12c and one atrial biological pacemaker 44 are depicted, it will be appreciated that fewer or more than these may be employed, and implanted in different heart locations, according to the heart condition and the desired therapy. For example, the pacemaker system may consist of a plurality of biological pacemakers in the left and/or right atrium and no biological pacemakers in one or both ventricles, or a plurality of biological pacemakers in the left and/or right ventricles and no biological pacemakers in one or both atria. Regardless of the heart regions in which the biological pacemakers are implanted, one or more biological pacemakers function as backup to one or more primary biological pacemakers. In the embodiment depicted in FIG. 3, the biological pacemakers 12a to 12c, and 44 together function as a backup system in the event that one of the biological pacemakers becomes ineffective due to advancing cardiac disease. The biological pacemakers that have backup pacing functions are suppressed until the occurrence of a particular arrhythmia such as a predetermined low heart rate. It has already been demonstrated that biological pacemakers can be overdrive-suppressed by electronic pacemakers, and take over pacemaker function, once the electronic pacemaker has been turned on as reported in, for example, *Circulation* 114(10):992-9 (2006).

The biological pacemakers 12 to 12c, and 44 may be implanted into a diseased heart, or into a heart experiencing normal or near-normal AV nodal conduction to prevent any immediate or potential arrhythmia. For example, the exemplary system depicted in FIG. 3 may be used to treat arrhythmia related to a disease such as sick sinus syndrome, which is one cause for symptomatic brady-arrhythmias, or Adam-Stokes attacks. The ventricular biological pacemakers 12a to 12c provide pacing only as a backup to the pacing functions performed by the atrial biological pacemaker 44. More particularly, although the atrial biological pacemaker 44 performs a primary pacing function as necessary, AV nodal block may progress to a point at which the right ventricle 18 unable to depolarize. In this or any other situation in which the atrial biological pacemaker 44 is not sufficiently effective, one of the ventricular biological pacemakers 12a to 12c will depolarize the right ventricle 18 at a predetermined pacing to assure sufficient cardiac output and avoid symptomatic brady-arrhythmias, including cardiovascular collapse.

The ventricular biological pacemakers 12a to 12c, or any other backup biological pacemakers that may be used in accordance with the present invention, are naturally suppressed in their function when the right ventricle 18 is conducting above a predetermined threshold pace. For example, the atrial biological pacemaker 44 is preferably designed to cause the right atrium 16 to conduct at a normal physiological rate of between 60 and 100 beats per minute at rest. When the heart is experiencing normal or near-normal AV nodal conduction, the right ventricle will also conduct at a physiological rate of 60 to 100 beats per minute at rest, and the function of the ventricular biological pacemakers is suppressed in the same manner that the heart's natural escape rhythm is naturally suppressed during normal heart rhythm. Under natural conditions, when AV nodal conduction is insufficient for the right ventricle 18 to depolarize, an escape rhythm is endogenously produced that causes the right ventricle 18 to autonomously depolarize at a pace of approximately 30 beats per minute. According to the present invention, at least one of the biological pacemakers 12a to 12c will be functional as the dominant ventricular pacemaker causing the right ventricle 18 and left ventricle (not shown) to depolarize at a higher rate than at the endogenous escape rhythm, the higher biological pacemaker-induced rate preferably ranging from about 45 to 50 beats per minute at rest.

As previously discussed, the biopacing system depicted in FIG. 3 includes a plurality of backup ventricular biological pacemakers 12a to 12c as an additional safety measure. In the event that heart experiences disease-based destruction, including infarcts, of certain heart regions where at least one of the ventricular biological pacemakers 12a to 12c is implanted, a backup ventricular biological pacemaker in a less deteriorated heart region will still be able to maintain pacing function. In an exemplary embodiment, the biological pacemakers are designed to have different pacing rates. For example, by controlling the type or amount of polynucleotide delivered to different heart regions, a plurality of biological pacemakers may be implanted, with each producing a unique pacing rate to decrease the likelihood of simultaneous activity originating from any two or more distinct biological pacemaker. Thus, a plurality of biological pacemakers may be introduced into any desired heart region to prevent or cure a particular arrhythmia, while mitigating the risk of the overall system being arrhythmogenic.

The biopacing system includes one or more backup biological pacemakers in or downstream in the conduction pathway from a heart region that is experiencing or may experience poor conduction. For example, if cardiac contraction is not being properly initiated by the SA node, the primary biological pacemaker and at least one backup biological pacemaker may be implanted in the myocardium of the right atrium to cause the right atrium to depolarize and create electric impulses that will travel to the AV node. Alternatively, if cardiac contraction is not being properly initiated by the SA node then the backup biological pacemakers may be implanted downstream in the conduction pathway from the right atrium, i.e. in the bundle of His, the Purkinje network, or one of the ventricles.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for preventing cardiac pacing dysfunction in a heart, comprising the steps of:

implanting into the heart an electronic pacemaker for producing primary pacing stimuli that modulate cardiac contraction; and implanting into the heart at least one biological pacemaker that is functionally suppressed when the electronic pacemaker is modulating cardiac function at a predetermined pacing rate, and further provides backup pacing stimuli when the electronic pacemaker is unable to modulate cardiac function at the predetermined pacing rate.

2. The method according to claim 1, wherein the step of implanting at least one biological pacemaker comprises implanting genetically engineered cells.

3. The method according to claim 1, wherein the step of implanting at least one biological pacemaker comprises implanting a delivery vector including a polynucleotide sequence.

4. The method according to claim 1, wherein the step of implanting at least one biological pacemaker comprises implanting genetically unmodified cells.

5. A method for preventing cardiac pacing dysfunction in a heart, comprising the steps of:
   implanting into an atrium of heart at least one primary biological pacemaker that produces primary pacing stimuli to modulate cardiac function; and
   implanting into a ventricle of heart at least one backup biological pacemaker that is suppressed when the primary biological pacemaker is modulating cardiac function at a predetermined pacing rate, and produces backup pacing stimuli when the primary biological pacemaker is unable to modulate cardiac function at the predetermined pacing rate.

6. The method according to claim 5, wherein the at least one primary biological pacemaker, when implanted, produces primary pacing stimuli at a first rate ranging between about 60 and about 100 beats per minute, and the at least one backup biological pacemaker, when implanted, produces backup pacing stimuli at a second rate that is lower than 60 beats per minute when the primary biological pacemaker is unable to modulate cardiac function at the first rate.

7. The heart pacing system according to claim 6, wherein the second rate for the backup pacing stimuli is between about 45 and about 50 beats per minute.

8. The method according to claim 5, wherein one or both of the steps of implanting at least one primary biological pacemaker and implanting at least one backup biological pacemaker comprise implanting genetically engineered cells.

9. The method according to claim 5, wherein one or both of the steps of implanting at least one primary biological pacemaker and implanting at least one backup biological pacemaker comprise implanting a delivery vector including a polynucleotide.

10. The method according to claim 5, wherein one or both of the steps of implanting at least one primary biological pacemaker and implanting at least one backup biological pacemaker comprise implanting a genetically unmodified cell.

11. A method for preventing cardiac pacing dysfunction in a heart, comprising the steps of:
   implanting into an atrium of the heart an electronic pacemaker for producing primary pacing stimuli that modulate cardiac contraction; and
   implanting into a ventricle of the heart at least one biological pacemaker that is functionally suppressed when the electronic pacemaker is modulating cardiac function at a predetermined pacing rate, and further provides backup pacing stimuli when the electronic pacemaker is unable to modulate cardiac function at the predetermined pacing rate.

12. The method according to claim 11, wherein the step of implanting at least one biological pacemaker comprises implanting genetically engineered cells.

13. The method according to claim 11, wherein the step of implanting at least one biological pacemaker comprises implanting a delivery vector including a polynucleotide sequence.

14. The method according to claim 11, wherein the step of implanting at least one biological pacemaker comprises implanting genetically unmodified cells.

* * * * *